United States Patent [19]
Nevel et al.

[11] Patent Number: 5,646,405
[45] Date of Patent: Jul. 8, 1997

[54] METHOD OF DETECTING CONTAMINANTS IN COTTON FIBERS

[75] Inventors: Avishai Nevel, Providence; Kendall W. Gordon, Jr., North Kingston, both of R.I.

[73] Assignee: Lawson-Hemphill, Inc., Central Falls, R.I.

[21] Appl. No.: 563,995

[22] Filed: Nov. 29, 1995

[51] Int. Cl.⁶ .................... G01N 21/71; G01N 33/36
[52] U.S. Cl. .................. 250/341.6; 250/330; 250/339.12
[58] Field of Search .................... 19/65 A; 250/341.6, 250/339.12, 330, 370.06

[56] References Cited

U.S. PATENT DOCUMENTS

| 5,123,144 | 6/1992 | Demuth et al. | 19/65 A |
| 5,489,778 | 2/1996 | Burmester et al. | 250/330 |

*Primary Examiner*—Carolyn E. Fields
*Attorney, Agent, or Firm*—Brian M. Dingman

[57] ABSTRACT

A method of determining the presence of contaminants in cotton fibers, including the steps of heating the cotton fibers, and analyzing infrared emanations from the heated cotton to determine areas within the cotton with non-cotton infrared signatures as indicative of contaminants in the cotton.

20 Claims, 2 Drawing Sheets

METHOD OF DETECTING CONTAMINANTS IN COTTON FIBERS

FIELD OF INVENTION

This invention relates to a method of determining contaminants in cotton fibers using machine vision.

BACKGROUND OF INVENTION

Raw cotton fiber is typically contaminated with contaminants such as seeds or other cotton-plant matter, and a sticky substance secreted in the cotton by insects, called "honeydew". Honeydew is the result of infestation of growing cotton by aphids or white-fly. It takes the form of randomly distributed droplets of highly concentrated sugars, causing cotton stickiness. Such contaminants should be removed from the cotton fibers to as great an extent as possible in order to provide a higher quality cotton yarn. Honeydew presents unique problems due to its stickiness. It has been found that honeydew fouls cotton fiber and cotton yarn processing equipment, which ultimately increases the cost of manufacturing products from cotton. Fouled equipment must be shut down and cleaned, causing production downtime. Additionally, the product produced from contaminated equipment can be a lower grade, and thus have a lower value.

It has thus been found to be important to test the cotton fiber, before it is spun into yarn, for the presence and the amount of various contaminants. Vegetative matter is easy to see, and can be removed by combing. Honeydew, however, cannot be seen. The current tests for honeydew include the following. One manner of testing for honeydew is to use a small-scale production machine, for example a cotton yarn spinner, and run a portion of each bale of cotton through the machine and then inspect the machine for fouling. The results can then be extrapolated to the production environment. This, however, requires expensive, specialized equipment which is dedicated for such testing, and also results in the fouling of this equipment, which must then be cleaned. Accordingly, this test is somewhat slow, unsatisfactory, and ultimately expensive.

A second test involves taking a sample from each bale of cotton and sandwiching it in metal foil, and then heating the foil in an oven above the flash point of cotton to burn off the cotton. The honeydew tends to char more than the cotton fibers. After heating, the foil sandwich is removed from the oven and opened. The cotton fiber ash can be blown away. However, the honeydew ash remains as black char spots on the foil. The area of such spots can then be determined as an approximate measure of the area of the cotton fiber sample that is contaminated with honeydew. This test requires a fair amount of manual labor, and is also somewhat subjective, making it a less than ideal solution to the honeydew test problem.

SUMMARY OF THE INVENTION

It is therefore an object of this invention to provide an improved test procedure for cotton fiber contaminants.

It is a further object of this invention to provide such a procedure which can be automated.

It is a further object of this invention to provide such a procedure which is more objective than existing procedures.

It is a further object of this invention to provide such a procedure which is less expensive to perform than other procedures.

It is a further object of this invention to provide such a procedure which is more effective in determining the presence of honeydew in cotton fiber.

It is a further object of this invention to provide such a procedure which is more effective at determining the amount of honeydew in cotton fiber.

It is a further object of this invention to provide such a procedure which does not require small scale production equipment for determining the presence of honeydew or other contaminants in cotton fiber.

This invention results from the realization that contaminants such as honeydew and vegetative matter in cotton fiber can be found based on the infrared signature of the contaminant. A sample of cotton is heated, and an infrared image of the heated cotton, taken either during the heating process or while the cotton is cooling, is captured. The contaminants are found based on their characteristic infrared emanation wavelengths, as compared to the different infrared emanation wavelength of the cotton itself. This determination can be automated to provide an automatic test for honeydew.

This invention features methods of determining the presence of contaminants such as honeydew and vegetative matter in cotton fibers. Most basically, the method contemplates heating the cotton fibers and analyzing infrared emanations from the heated cotton to determine areas within the cotton with non-cotton infrared signatures as indicative of contaminants in the cotton.

The infrared analysis may be accomplished with at least one infrared camera which captures an infrared image of the heated cotton. The infrared imaging may take place while the cotton is being heated, or while the cotton is cooling. The infrared signature of a contaminant may be defined as the wavelength or wavelengths at which the contaminant radiates, likely determined at a given temperature, or a given time after heating has been commenced or cooling has begun. It is likely that characterization of contaminants may be more unequivocally determined by taking multiple, temporally-spaced infrared images of the heated cotton so that contaminants can be identified as either heating or cooling at a different rate than the cotton fibers.

The relevant infrared signatures of the contaminant or contaminants being monitored can be determined a priori. This information can then be used by the operator to determine the presence of the contaminant, and the area of the cotton fibers imaged in which the particular contaminant is found. Alternatively, this information can be programmed into a computer for automated analysis of the presence and level of contaminants. This may be accomplished, in one case, by assigning different computer output (e.g. printer or monitor) parameter values to different sensed infrared wavelengths, or wavelength ranges. For example, the different wavelength ranges within the total infrared wavelength range sensed may be assigned different colors for a color output, which may be accomplished with a computer monitor. Or, other video image pixel values may be assigned to the infrared image. For example, gray scale values may be assigned. This information can then be displayed for an operator and/or automatically analyzed for the presence and amount of contaminants within the imaged area. The amount of contaminants can be determined by determining the relative area of the image emanating at the wavelength or wavelengths determined to be contaminant wavelengths. The amount of contaminant may be automatically calculated by counting the number of pixels emanating at the predetermined contaminant wavelength, as compared to the total number of pixels in the entire image, or as compared to the number of pixels which are determined to be from uncontaminated cotton. This can be done either with or without an actual display.

The heating and imaging may be automated or not. The test may be manually accomplished by providing a heating zone, for example an electric, gas or microwave oven, in which samples are placed and heated as desired. The samples may then be manually or automatically removed from the oven and placed in front of an infrared camera, whose output is displayed and/or analyzed as described above. Or, the camera may take the image directly from the oven. The test may be further automated by providing a heating zone and one or more infrared cameras mounted near the heating zone, and then automatically moving cotton fiber samples through the heating zone and past the camera (s). This movement may be accomplished in a desired fashion, for example with a conveyor belt or similar equipment. The movement may be accomplished continuously, or in a step-wise fashion so that the samples remain in the heating zone, and remain still in the focal plane of the infrared camera or cameras, for the desired amount of time. Other equivalent methodologies are considered within the scope of this invention.

BRIEF DESCRIPTION OF THE DRAWINGS

Other objects, features and advantages will occur to those skilled in the art from the following description of a preferred embodiment and the accompanying drawings, in which.

DESCRIPTION OF THE PREFERRED EMBODIMENT

This invention is accomplished in an inexpensive, machine-vision test for determining the presence and level of contaminants in cotton fiber. The invention is particularly adapted to sensing honeydew in cotton fiber, but this is not a limitation of the invention, as the invention may be used to find any contaminant that has an infrared signature which is different than that of the cotton fibers. The difference in infrared signature is believed to be due to different heating/ cooling rates of cotton and the contaminants.

The contaminants are sensed by heating the cotton fibers which are suspected of including contaminants, and analyzing infrared (IR) emanations from the heated cotton to determine areas within the cotton with non-cotton infrared signatures as indicative of contaminants in the cotton. The particular types of contaminants may have their infrared signatures determined in advance, for the particular test conditions, so that the contaminants in a tested cotton sample can be identified. The relative amount of contaminants may be determined by comparing the area with non-cotton infrared signatures to the total area tested.

Preferably, an IR camera is used to image the heated yarn, either while it is being heated, while it is being held at a desired temperature, or while it is cooling. Different values can be assigned to different wavelengths, or different wavelength regions, of the camera output. For example, different colors may be assigned to different wavelength regions or bands, or gray scale values may be assigned to the different wavelengths. The assigned values for each pixel can then be provided to a video monitor for viewing and analysis by an operator, and/or provided to a computer for automated contaminant analysis. The automation may be accomplished by programming the computer with the predetermined contaminant signatures, and then comparing the IR camera output to this predetermined data. The total area of any one or more contaminants within the field of view of the camera may be determined by any method which can determine areas based on the difference in the camera output value for the contaminants versus the pure cotton fiber areas. One manner in which this may be accomplished is to count the number of pixels with non cotton-fiber emanations, and compare that number of pixels to the total number of camera pixels, or the total area of the imaged cotton, as a measure of the amount of cotton which is contaminated.

The methodology thus allows non-contact, machine-vision testing of raw cotton fibers for contaminants, particularly honeydew, without the need for testing on small scale production equipment or testing by the burn method described above. The result is a faster, less expensive, more accurate test which may be performed on each bale of cotton to determine its suitability for use in cotton processing equipment.

Figure 1:
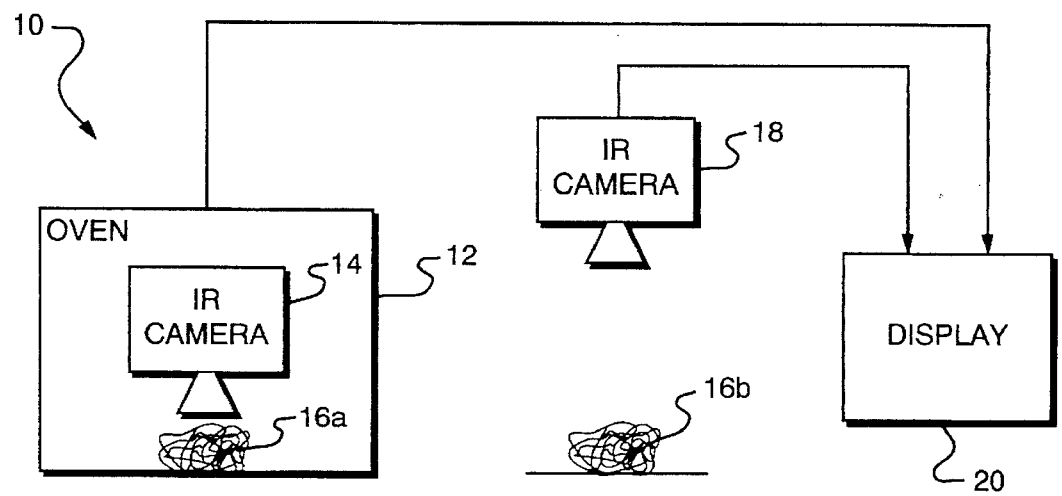
FIG. 1 is a schematic diagram of a manual method of determining the presence of contaminants in cotton fibers according to this invention.

There is shown in FIG. 1 in simplified schematic form test system 10 which can be used to manually practice the methods of this invention. System 10 includes oven 12 which may be any type of oven which can heat cotton sample 16a, including convection and conduction ovens, and microwave ovens, for example. Cotton samples such as sample 16a may be imaged by IR camera 14 within or exposed to the inside of oven 12, either while it is being heated, or while it is being maintained at a desired temperature, or after it has been heated and is cooling toward ambient temperature. The output from camera 14 is provided to display 20 for operator analysis of the image.

Alternatively, IR camera 18 may be mounted outside of oven 12 and used to image cotton fiber sample 16b after it is removed from oven 12. One image, or temporally spaced multiple images of the cotton sample, can be taken and displayed on display 20. The multiple displays may be simultaneous or not, as desired.

Contaminants in cotton sample 16a or 16b are determined based on their infrared signature. It has been found that honeydew tends to radiate in the infrared region at a different wavelength than the cotton in which it is found, while the cotton sample is cooling from an elevated temperature. Thus, if a sample of cotton with honeydew contaminant is heated in an oven and then removed from the oven and placed in front of an infrared camera, while the sample is cooling the infrared emanation wavelength of honeydew is different than that of uncontaminated cotton fiber. Display 20 may be enabled to assign different video image pixel values to different sensed wavelengths, or sensed wavelength bands, as a means to display the different sensed wavelengths. Two examples of such pixel values are color for a color monitor, and gray scale value for a black and white monitor. The image or images of the samples can be examined by the operator to determine the presence of the characteristic color or gray scale value indicative of any one or more contaminants which have been precharacterized. The display may include one or more images of standard or acceptable quality cotton fiber samples to allow direct visual comparison for cotton fiber quality grading purposes.

Figure 2:
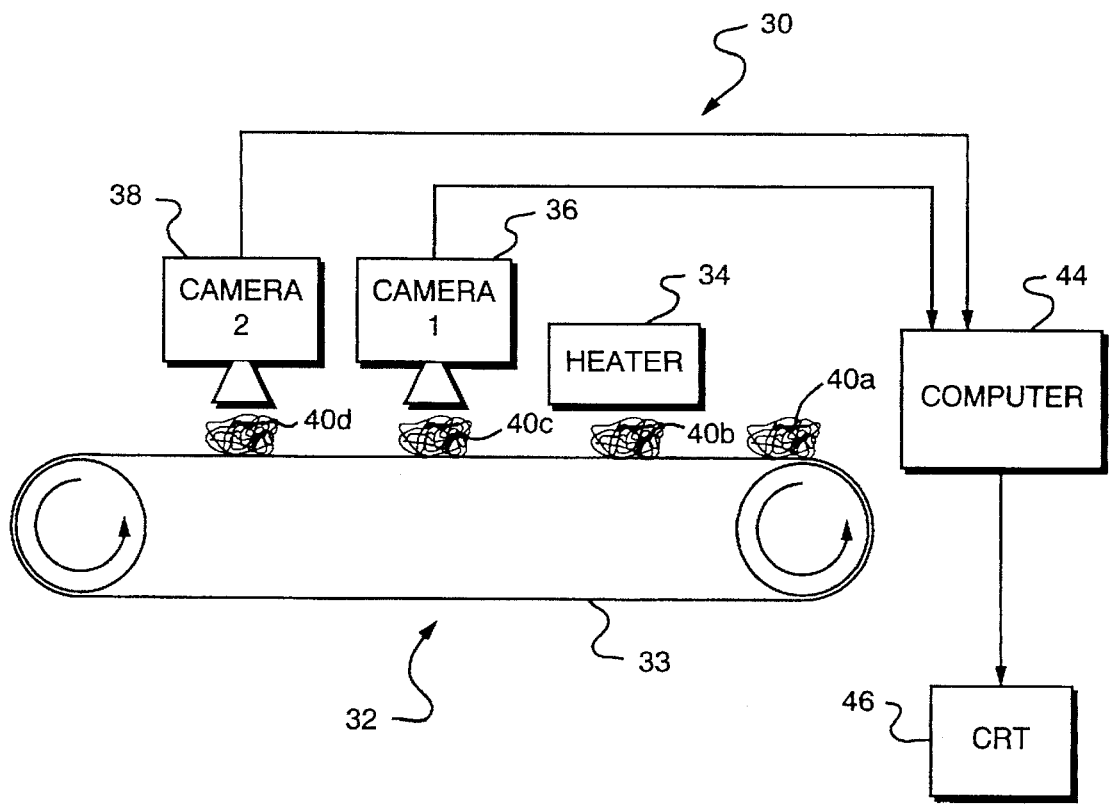
FIG. 2 is a schematic diagram of a more automated method which accomplishes contaminant detection and contaminant area determination automatically.

The above-described test may be more automated by using system 30, FIG. 2. In system 30, the cotton fiber samples under test are moved automatically through a heating zone and then an IR imaging zone using an automated drive such as conveyor belt drive 32 including belt 33 which is shown as carrying cotton fiber samples 40a through 40d. Samples to be tested are placed upstream of the heater as shown by sample 40a, and then move under heater 34 as shown by sample 40b. The dwell time in the heating zone within or underneath heater 34 is appropriate to heat the cotton sample to a desired level. Sample 40c is then imaged a first time by IR camera 1, number 36. The camera output is provided to computer 44. For situations in which it is desirable to obtain temporally-spaced images, a second IR camera 2, number 38, may be provided downstream of camera 1. The output of camera 2 is also provided to computer 44. Alternatively, temporally-spaced images may be accomplished with a single camera if the cotton fiber drive is stopped for sufficient time while the cotton sample is in the imaging zone of the camera. This may be accomplished by the use of stepper motors or any other desirable manner.

As described above, computer 44 may be programmed to automatically determine the presence of, and amount of, contaminants in the cotton. A preferred method of determining the amount of honeydew in cotton is described below in conjunction with the flow chart of FIG. 3. Briefly, the infrared signature of contaminants which may be encountered in cotton fiber are characterized, for the particular test conditions, before the operation of the test system. The characterization can include the infrared emanation wavelength or wavelengths of the contaminants at particular temperatures, or while being held at a particular temperature, while being heated to a particular temperature, or while cooling from a particular temperature.

As the heating and cooling rate of many contaminants is different from that of pure cotton, contaminants may potentially be more unequivacably characterized with temporally-spaced images that are compared to determine the temperature of each region of the image based on its IR emanation wavelength. For example, it appears that honeydew cools more slowly than pure cotton fibers. Accordingly, if a honeydew-contaminated cotton fiber sample is heated above ambient temperature and then imaged at more than one time while it is cooling back to ambient temperature, the presence of honeydew may be determined based on differential cooling rate, determined from the change over time of the infrared wavelength of emanations from the honeydew, as compared to that of the surrounding pure cotton. Alternatively, the differential cooling rate may be sensed with one IR image by determining the temperatures of different regions of the heated sample while the sample is cooling but before it reaches ambient temperature—at any given time, the temperature of regions which include honeydew contamination should be greater than the temperature of surrounding regions of pure cotton fiber, due to the faster cooling rate of the cotton fiber.

Most commercially available infrared cameras, for example the Compix 6000 series, Compix, Inc., Tualatin, Oreg., include the ability of adjusting the output signal so that regions emanating in different wavelengths are differently colored on a color monitor, or of different gray scale value in a black and white monitor. The output of each pixel of the camera may be assigned a pixel value which is related to the infrared wavelength (temperature) captured by the pixel. The different wavelengths will then show up as different colors or shades of gray in the display, which may then be analyzed by the operator. Additionally, computer 44 may be pre-programmed to determine the area of the entire image with a particular contaminant by counting the number of pixels emanating at the contaminant emanation wavelength. When the camera output has been modified by the assignment of different pixel values as described above, computer 44 can be programmed to look for the desired contaminant pixel values. The camera output may also be displayed to the operator on CRT 46.

Figure 3:
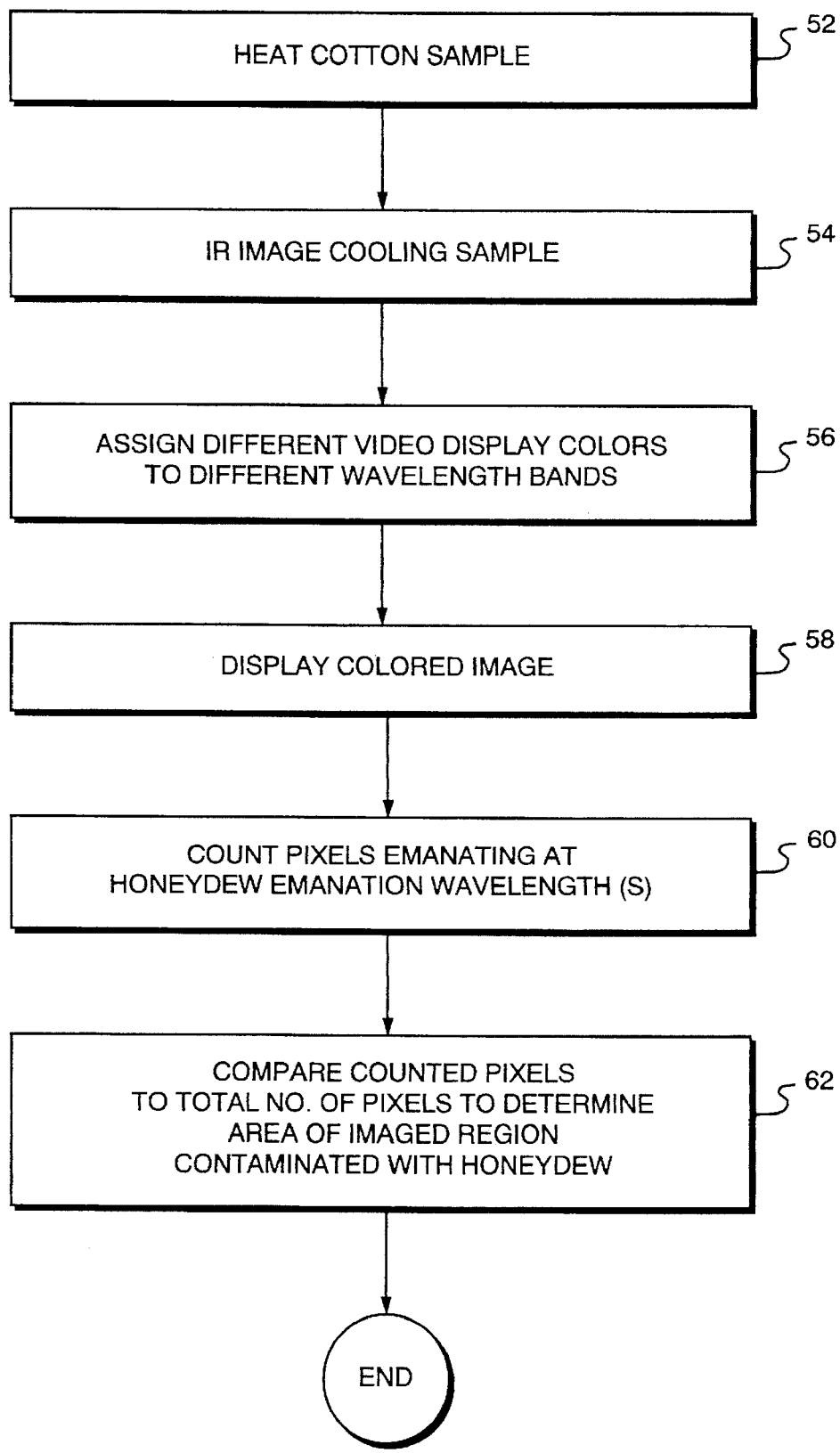
FIG. 3 is a flow chart of one manner of automatically determining contaminant presence and quantity using an apparatus such as that shown in FIG. 2.

Flow chart 50, FIG. 3, details an embodiment of the methodology for determining the amount of honeydew in a cotton sample using an apparatus such as that disclosed in FIG. 2. The cotton sample is heated, step 52, and then one or more infrared images of the cooling sample are captured, step 54. Different video display colors are assigned to different wavelength bands of the captured image, step 56, and the colored image is displayed, step 58. This display is optional in an automated system. Computer 44, FIG. 2, is then enabled to count the number of pixels, either of the camera output, or of the display, which were emanating at the wavelength or wavelengths at which honeydew has been determined to emanate. The specific wavelength is dependent on the process conditions, for example the temperature of the heating zone, the amount of time the sample is in the heating zone, the amount of time that the sample has been out of the heating zone, and the ambient temperature. This information is taken into account in the pre-characterization of the honeydew emanation wavelengths which are programmed into the computer. A comparison is then made of the number of such counted pixels to the total number of pixels in the camera output or display, as appropriate, to determine the area of the imaged region which is contaminated with honeydew. For example, if 100 out of 1,000 pixels are emanating at the honeydew emanation wavelength, the contaminant level would be determined to be 10%.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A method of determining the presence of contaminants in cotton fibers, including the steps of:

heating the cotton fibers; and analyzing infrared emanations from the heated cotton, including determining areas of the cotton emanating at different infrared wavelengths than the cotton fibers to determine areas within the cotton with non-cotton infrared signatures as indicative of contaminants in the cotton.

2. The method of claim 1 in which the contaminants include honeydew.

3. The method of claim 1 in which the step of analyzing the infrared emanations of the heated cotton includes taking at least one infrared image of the heated cotton.

4. The method of claim 3 in which the step of taking at least one infrared image of the heated cotton includes taking multiple, temporally-spaced images of the heated cotton.

5. The method of claim 3 in which the step of taking at least one infrared image of the heated cotton includes infrared imaging the cotton while it is being heated.

6. The method of claim 3 in which the step of taking at least one infrared image of the heated cotton includes infrared imaging the cotton while it is cooling.

7. The method of claim 1 in which the step of analyzing infrared emanations from the heated cotton includes analyzing infrared emanations from the cotton while it is being heated.

8. The method of claim 1 in which the step of analyzing infrared emanations from the heated cotton includes analyzing infrared emanations from the cotton while it is cooling.

9. The method of claim 1 in which the step of heating the cotton fibers includes radiatively heating the cotton.

10. The method of claim 1 in which the step of heating the cotton fibers includes passing the cotton fibers through a heating zone.

11. The method of claim 10 in which the step of analyzing infrared emanations from the heated cotton includes infrared imaging the cotton after it is passed through the heating zone.

12. The method of claim 11 in which the step of infrared imaging the cotton includes providing an infrared camera downstream of the heating zone.

13. The method of claim 1 in which the step of analyzing infrared emanations from the heated cotton includes infrared imaging the cotton with an infrared camera.

14. The method of claim 13 in which the step of analyzing infrared emanations from the heated cotton further includes creating a display from the infrared camera.

15. The method of claim 14 in which the step of creating a display from the infrared camera includes assigning different colors to different infrared wavelengths captured by the camera.

16. The method of claim 14 in which the step of creating a display from the infrared camera includes creating a video image from the infrared camera, in which the video image pixel values are related to the infrared wavelengths captured by the camera.

17. The method of claim 1 in which the step of analyzing infrared emanations from the heated cotton includes determining the relative area of the determined areas emanating at different infrared wavelengths than the cotton fibers.

18. A method of determining the presence of contaminants in cotton fibers, including the steps of:

heating the cotton fibers, and then cooling the heated cotton fibers;

capturing an infrared image of the heated cotton while it is cooling;

assigning different output parameter values to different infrared wavelengths of the captured image; and analyzing the output parameter values to determine areas within the cotton with non-cotton emanated infrared wavelengths as indicative of contaminants in the cotton.

19. The method of claim 18 in which the step of assigning different output parameter values to different infrared wavelengths of the captured image includes assigning at least one display color to non-cotton emanated infrared wavelengths.

20. A method of determining the presence of honeydew in cotton fibers, including the steps of:

providing a cotton fiber heating zone;

providing an infrared camera proximate the cotton fiber heating zone;

moving cotton fiber first through the heating zone, and then within the imaging area of the infrared camera while the heated cotton is cooling, and still above ambient temperature;

capturing an infrared image of the cooling cotton with the infrared camera; and analyzing the captured infrared image, including determining areas of the cotton emanating at different infrared wavelengths than the cotton fibers, to determine areas within the cotton with non-cotton infrared signatures as indicative of honeydew contamination in the cotton.

* * * * *